US006365340B1

(12) United States Patent
Wheeler

(10) Patent No.: US 6,365,340 B1
(45) Date of Patent: Apr. 2, 2002

(54) DETECTION OF PROSTATITIS

(76) Inventor: Ronald E. Wheeler, 412 C.R. 243, P.O. Box 217, Durango, CO (US) 81302

( * ) Notice: Subject to any disclaimer, the term of this patent is extended or adjusted under 35 U.S.C. 154(b) by 0 days.

(21) Appl. No.: 09/438,722

(22) Filed: Nov. 11, 1999

Related U.S. Application Data

(60) Provisional application No. 60/107,996, filed on Nov. 11, 1998.

(51) Int. Cl.[7] .................................................. C12Q 1/00
(52) U.S. Cl. ............................... 435/4; 435/7.4; 435/19; 435/287.7; 435/287.9; 435/970; 436/518; 436/524; 436/810; 436/823; 530/380
(58) Field of Search ............................... 435/4, 7.4, 19, 435/287.7, 287.9, 970, 7.23; 436/518, 524, 810, 823; 530/380

(56) References Cited

U.S. PATENT DOCUMENTS

| 3,712,853 A | | 1/1973 | Rittersdorf et al. |
| 4,301,115 A | | 11/1981 | Rapkin et al. |
| 4,637,979 A | | 1/1987 | Skjold et al. |
| 4,645,842 A | | 2/1987 | Corey |
| 4,657,855 A | | 4/1987 | Corey et al. |
| 4,703,017 A | | 10/1987 | Campbell et al. |
| 4,704,460 A | | 11/1987 | Corey |
| 4,716,236 A | | 12/1987 | Ward et al. |
| 4,758,508 A | | 7/1988 | Schnabel et al. |
| 4,774,340 A | | 9/1988 | Corey et al. |
| 5,656,448 A | * | 8/1997 | Kang et al. |
| 5,663,044 A | | 9/1997 | Noffsinger et al. |
| 5,776,780 A | | 7/1998 | Smith et al. |
| 5,972,594 A | | 10/1999 | Heine |

OTHER PUBLICATIONS

Persson et al., Journal of Urology. vol. 155, pp. 958–960, Mar. 1996.*

Wright et al., Journal of Urology. vol. 152, pp. 2300–2303, Dec. 1994.*

Nickel et al., (1998) *Urology*, "Diagnosis and Treatment of Prostatitis in Canada," 52:797–802.

McNaughton et al., (1998) *The Journal of Urology*, "How Common is Prostatitis? A National Survey of Physician Visits," 159:1224–1228.

Holan K. et al., (1997) *Veterinary Clinical Pathology*, "Clinical Evaluation of a Leukocyte Esterase Test–Strip for Detectino of Feline Pyuria," 26:126–131.

Takamoto, H. et al., (1987) *Abstract*, "Clinical Studies of Chronic Prostatitis the pH and Leukocyte Counts of Expressed Prostatic Secretions in Prostatitis," 48:1525–1531.

* cited by examiner

Primary Examiner—Bao-Thuy L. Nguyen
(74) Attorney, Agent, or Firm—DeWitt Ross & Stevens S.C.; Charles S. Sara

(57) ABSTRACT

The present invention is directed to a method of detecting prostatitis comprising obtaining an expressed prostatic secretion from a patient; contacting a device having diagnostic test reagents to the expressed prostatic secretion, the diagnostic test reagents reacting with the expressed prostatic secretion to produce a change in the device; reading the change in the device to produce a positive or negative experimental test result, wherein the experimental test result is positive when the experimental test result is predetermined to correspond with a number above 10 for the number of white blood cell per high powered field and the experimental test result is negative when the experimental test result corresponds with a number of 10 or less for the number of white blood cell per high powered field; and determining presence of prostatitis with the positive experimental test result and the absence of prostatitis with the negative experimental test result. The present invention is also directed to a device for use in the inventive method. The device has two indicators, one for the presence of prostatitis and one for the absence of prostatitis.

14 Claims, No Drawings

DETECTION OF PROSTATITIS

PRIORITY INFORMATION

Priority is hereby claimed to provisional application Ser. No. 60/107,996, filed on Nov. 11, 1998, which is incorporated herein by reference.

FIELD OF THE INVENTION

The present invention relates to a device and process for detecting prostatitis.

DESCRIPTION OF THE RELATED ART

The prostate gland (or prostate) is a walnut-sized, mucous-producing organ in males that lies just below the urinary bladder. The prostate typically grows and enlarges throughout life. The only known function of the prostate is to produce a secretion that nourishes and protects the sperm during reproduction. The urethra, the canal that in most mammals discharges urine from the bladder, passes through the prostate gland. Unfortunately, this anatomical feature creates problems, often associated with difficulty in urination, as males age.

A national survey of U.S. physician visits estimated that the diagnosis of prostatitis results in 2 million office visits per year in the United States and is the most frequent diagnosis resulting in an office visit to urologists in men less than 50-years-old. Collins, M. M., et al. (1998) *J. Urol.* 159:1224–1228. Prostatitis is defined as an inflammation or infection of the prostate gland. While prostatitis may be acute, associated with systemic findings of fever, chills and rigors, most cases of prostatitis are chronic and tend to be incurable with relatively frequent recurrences despite optimal standard therapy. Chronic prostatitis (inflammation or infection of the prostate) is common to all adult men. It is associated with virtually all cases of prostate cancer and is present in every prostate biopsy regardless of other findings. Chronic prostatitis may not cause significant symptoms in many men, but in others it can be a devastating disease that severely affects the quality of life of those afflicted. It is difficult to diagnose and even more difficult to treat.

The most common symptom of chronic prostatitis is pelvic pain, followed by various voiding symptoms, impotence, and infertility. Pain from prostatitis is usually located in the groin, testicles, and penis, just above the rectum or in the suprapubic area over the bladder. Pain is frequently associated with ejaculation. Typical voiding symptoms produced by prostatitis include getting up at night to void (nocturia), frequency and urgency of urination, incomplete voiding, decreased force of the urinary stream, intermittency of the stream, and a need to push or strain to void. Impotence or erection difficulties and male infertility are also associated with prostatitis.

Conventional methods of detecting prostatitis include a digital rectal examination, midstream specimen of urine, specific culture, urine dipstick, and ejaculate culture. Other methods include the AUA Symptom Score, which is a survey that was drafted by the American Urologists Association and was validated in 1996. It evaluates a man's voiding abilities. Symptom Score survey includes questions on nocturia, frequency, intermittency, incomplete elimination, stream size, urgency, and the need to strain. Respondents answer seven questions about the severity of symptoms. Respondents indicate the frequency of the events, with each frequency having an assigned score, and a diagnosis is made.

Still another method is the prostate specific antigen (PSA) test, which is a blood test that can be used to detect prostatitis. PSA is a protein substance produced by certain cells in the prostate gland. A very small amount of PSA escapes into the blood stream. Thus, PSA can be tested in the blood. Because the amount of PSA in the blood is very low, detection of it requires a very sensitive monoclonal antibody technique.

Still yet another test is one that examines expressed prostatic secretion (EPS), which is a secretion, not a body fluid. Traditionally, EPS was tested through a microscopic examination of the EPS. The prostatic secretion is obtained by gentle massage of the prostate during the digital rectal examination. When the secretion is examined under the microscope, a finding of more than 10 white blood cells per high powered field (WBCS/HPF) is considered definitive proof of inflammation and prostatitis.

While all of these tests are available, Nickel, et al. report that only 18% of primary care physicians (PCPs) and 41% of urologists said that they employed any type of specific prostate tests. Nickel, et al. (1998) *Urology* 52(5) 797–802. Nickel, et al. conclude from a survey of PCPs and urologists that there is widespread frustration, discomfort, and a lack of confidence in their perceived ability to manage prostatitis. Specifically, physicians have expressed a high degree of frustration and unhappiness in dealing with prostatitis, which was driven by a lack of confidence and comfort in their ability to accurately diagnose and subsequently rationalize treatment of prostatitis. The surveyed physicians expressed a desire for a simpler and clearer diagnostic guidelines.

Simpler and clearer diagnostic guidelines are provided by the invention described herein. The invention includes a method for detecting prostatitis using a device, such as a dipstick, to test for white blood cells in EPS. Dipsticks are currently used to test for multiple analytes, such as glucose and protein. For example, a dipstick that detects neutrophil defensins to diagnose reproductive tract inflammation and preeclampsia is described in U.S. Pat. No. 5,972,594 to Heine.

Dipsticks and related components that detect leukocytes and leukocyte enzymes in body fluids have been patented. For example, U.S. Pat. No. 4,758,508 to Schnabel, et al. describes an agent and a method for detecting esterolytic and/or proteolytic enzymes in body fluids. U.S. Pat. No. 4,637,979 to Skjold, et al. describes a composition and test device for determining the presence of leukocytes in test samples including body fluids such as urine. U.S. Pat. No. 4,645,842 describes pyrrole compounds, and U.S. Pat. No. 4,704,460 (both to Corey) describes novel compounds for detecting the presence of hydrolytic analytes including leukocytes, esterase, and protease, in a test sample, including urine. U.S. Pat. No. 4,774,340 to Corey describes a method for preparing 3-hydroxy pyrroles and esters thereof, which are used to test samples including urine. A composition and test device for determining the presence of leukocytes, esterase, and protease in a body fluid including urine is described in U.S. Pat. No. 4,657,855 to Corey, et al. A method for determining the concentration of white blood cells in urine or other biological fluid is described in U.S. Pat. No. 5,663,044 to Noffsinger, et al. A method for preparing an ester used to detect leukocyte cells, esterase, and protease in body fluids such as urine is described in U.S. Pat. No. 4,716,236 to Ward, et al. All of these patents, which are incorporated herein by reference, correlate an abnormally high level of leukocytes in a patient's urine with the possible indication of pathological conditions such as kidney or urogenital tract infection or other dysfunction.

However, none of the above-noted approaches provides a rapid and economical method of detecting prostatitis. More particularly, none of these use EPS as a test sample. Such a method, described herein, provides a rapid and economical method for detecting prostatitis.

SUMMARY OF THE INVENTION

A principal aim of the invention is to provide a method for detecting prostatitis that includes using a device, such as a dipstick, to test expressed prostatic secretion (EPS).

A further aim of the present invention is to provide a device, such as a dipstick, for detecting prostatitis that includes an indication of the presence or absence of prostatitis.

In short, the invention described herein is directed to a method of detecting prostatitis comprising obtaining an expressed prostatic secretion from a patient; contacting a device having diagnostic test reagents to the expressed prostatic secretion, the diagnostic test reagents reacting with the expressed prostatic secretion to produce a change in the device; reading the change in the device to produce a positive or negative experimental test result, wherein the experimental test result is positive when the experimental test result is pre-determined to correspond with a number above 10 for the number of white blood cell per high powered field and the experimental test result is negative when the experimental test result corresponds with a number of 10 or less for the number of white blood cell per high powered field; and determining presence of prostatitis with the positive experimental test result and the absence of prostatitis with the negative experimental test result.

The invention also provides a device for detecting prostatitis from an expressed prostatic secretion using a dipstick comprising a matrix having diagnostic test reagents that react with the expressed prostatic secretion by detecting leukocytes or a leukocyte enzyme, the matrix having two portions, wherein a first portion indicates the presence of prostatitis and a second portion indicates the absence of prostatitis; a mounting substrate, the matrix attached to the mounting substrate, wherein the device produces a visual change in the matrix upon contact of the matrix with the expressed prostatic secretion, the first indicator producing a positive experimental test result, and the second indicator producing a negative experimental result; wherein the experimental test result is positive when the experimental test result is pre-determined to correspond with a number above 10 for the number of white blood cell per high powered field and the experimental test result is negative when the experimental test result corresponds with a number of 10 or less for the number of white blood cell per high powered field; and wherein the test device determines the presence of prostatitis with the positive experimental test result and the absence of prostatitis with the test negative experimental result.

Described herein is a method to detect rapidly and economically prostatitis using a device (preferably a dipstick) to test expressed prostatic secretion (EPS). EPS is a secretion, not a body fluid. Traditionally, EPS was examined microscopically. If more than 10 WBCS/HPF were detected with the microscope, a diagnosis of prostatitis resulted. The subject invention tests EPS with a device that has diagnostic test reagents that detect leukocytes and/or leukocyte enzymes. Study results show that the subject invention provides test results that correlate 97.5% with test results obtained through conventional microscopy. Patient examples indicate that testing EPS, as opposed to bodily fluids such as ejaculate and urine, provides more accurate detection of prostatitis. Thus, EPS is a better indicator of prostate health than bodily fluids such as ejaculate.

Of particular utility is that the subject invention provides a method for detecting prostatitis that is faster and more economical when compared to conventional methods of testing for prostatitis. The subject invention eliminates the need for a microscope and provides a more accurate diagnosis for prostatitis. Because microscopes will no longer be needed to diagnose prostatitis, the subject invention reduces the laboratory procedure for these assays from a cumbersome counting procedure requiring microscopic observation, to a rapid, facile dip-and-read operation. Furthermore, this invention permits testing of prostatitis in areas that do not have the necessary equipment, reduces the costs associated with testing for prostatitis, and provides physicians with the confidence and ability to accurately diagnose prostatitis.

Further aims, objects, and advantages of the invention will become apparent upon a complete reading of the Detailed Description and attached claims, which follow.

DETAILED DESCRIPTION OF THE INVENTION

The invention uses expressed prostatic secretion (EPS) as the test sample. EPS is not a body fluid, such as urine or blood. Instead, EPS is a secretion. EPS does not move around and does not flow. It actually has characteristics more like mucus. EPS is present within the prostate intracellularly and intraductually. The EPS sample is obtained by gentle massage of the prostate during the digital rectal examination during which the prostate is pressed upon, and the EPS is expressed. Traditionally, the secretion was examined under the microscope. A finding of more than 10 white blood cells per high powered field (WBCS/HPF) was considered definitive proof of inflammation and prostatitis.

A first embodiment of the invention is a method for detecting prostatitis using a device, such as a dipstick, having diagnostic test reagents to detect prostatitis. The diagnostic test reagents react with the test sample to produce a change upon contact with the EPS. The test sample is EPS. Test results showed a 97.5% correlation between (1) conventional prostatitis detection using a microscope to count the number of leukocytes in an EPS sample and (2) the subject invention, which uses a device to detect leukocytes and/or leukocyte enzymes in an EPS sample. A second embodiment of the invention is a device, such as a dipstick, that has (1) a positive indication for the presence of prostatitis and (2) a negative indication for the absence of prostatitis. The difference between the positive indication and the negative indication is pre-determined.

The method: The subject method begins with obtaining a EPS sample from a symptomatic patient. Symptomatic patients are identified as described below. Once the sample is obtained, a device having diagnostic test reagents that detect leukocytes and/or a leukocyte enzyme is contacted with the EPS. Depending on the type of device used, a certain amount of time might have to pass before the device is read. For example, when using a MULTISTIX-2 by Bayer Aktiengesellschaft (Fed. Rep. Germany) two minutes pass between the time that the device is contacted with the sample and when it is read to produce an experimental test result. The MULTISTIX-2 dipstick is sold to test urine. In the subject method, it is used to test EPS. The experimental test result is then compared to pre-determined test results that indicates either the presence or absence of prostatitis.

The subject method can use a quantitative device (such as the MULTISTIX-2, MULTISTIX-10, URISTIX-4, or any leukocyte-detecting device) or the subject inventive device that has two indications, one for a positive result and one for a negative result. When using a quantitative device, it produces a range of results. For example, the MULTISTIX-2 produce quantitative results of 0, trace, +1, +2 and +3. Quantitative results also include "Between +1 and +2" and "Between +2 and +3." A test result of 0, trace, and +1 corresponds to 10 or less WBCS/HPF (i.e., the absence of prostatitis). A test result of Between +1 and +2, Moderate (+2), Between +2 and +3, and Large (+3) corresponds to greater than 10 WBCS/HPF (i.e., the presence of prostatitis). The pre-determination is done using a study such as the one detailed below in the Test Example. When the experimental test result correlates to 10 or less WBCS/HPF, this leads to a indication of an absence of prostatitis. Conversely, when the experimental test result correlates to more than 10 WBCS/HPF, this leads to an indication of a presence of prostatitis.

Symptomatic patients are identified using the Lower Tract Symptom Survey reprinted below. Symptomatic patients can also be selected based on a number of different criteria. For example, the AUA Symptom Score, mentioned above, can be used. Prostatitis patients generally are symptomatic, exhibiting significant voiding symptoms. Likewise, it would not be unusual for men with prostatitis to have an elevated PSA. Any of the criteria listed in the Related Art section or any other known in the art can be used with equal efficiency to identify symptomatic patients.

The device: The subject device used in the subject invention includes (1) a matrix (preferably filter paper) with diagnostic test reagents and (2) a mounting substrate (preferably polystyrene film), which typically does not absorb the test sample, such that the user can hold onto the substrate without contacting the sample. The device produces a visual change in the matrix upon contact with EPS. The matrix has two indicators-a first that indicates the presence of prostatitis and a second that indicates the absence of prostatitis. The first indicator produces a positive experimental test result and the second indicator produces a negative experimental result. The experimental test result is positive when the experimental test result is pre-determined to correspond with a number above 10 WBCS/HPF. Conversely, the experimental test result is negative when the experimental test result is pre-determined to correspond with a number of 10 or less WBCS/HPF. The subject device determines the presence of prostatitis with the positive experimental test result and the absence of prostatitis with the negative experimental test result.

The diagnostic test reagents may be associated with the matrix by any physical or chemical means, including, for example impregnation, coating, linking, and covalent attachment. The matrix may take any convenient physical form, such as a card, pad, strip, or dipstick. The diagnostic test reagents detect leukocytes and/or a leukocyte enzyme, such as leukocyte esterase, and esterolytic and proteolytic enzymes. Such diagnostic test reagents include the compositions of the above-referenced patents, including an ester (preferably a chromogenic ester) and a diazonium salt such as those described in U.S. Pat. No. 4,637,979. Another preferred reagent is a derivatized pyrrole amino acid ester, a diazonium salt, a buffer, and non-reactive ingredients as described in U.S. Pat. Nos. 4,645,842; 4,637,979; 4,657, 855; 4,704,460; 4,758,508; and 4,774,340. The preferred amounts of these ingredients is based on dry weight at the time of impregnation and is as follows: about 0.4% w/w derivatized pyrrole amino acid ester, about 0.2% w/w diazonium salt, about 40.9% w/w buffer, and about 58.5% w/w non-reactive ingredients.

The inventive device has one indication of the presence of prostatitis and a second indication for the absence of prostatitis. The two indications preferably are a negative (−) symbol and a positive (+) symbol, but could be any two indications. One embodiment of the device has the negative indication (e.g., the "−" portion of a possible "+" symbol) containing reagents that reacts with all samples. That is, the diagnostic test reagents react to some constituent analyte, such as urobilinogen, which is present in all samples. Alternatively, the diagnostic test reagents test an aspect of the sample, such as pH, that every sample has. The positive indication (e.g., the "|" portion of a "+" symbol) contains a reagent that the reacts only with samples containing a count of more than 10 WBCS/HPF. Another embodiment has the negative indicator (e.g., the "−" portion of a possible "+" symbol) having a higher sensitivity to leukocytes or a leukocyte enzyme such that it reacts to samples containing any number of leukocytes. The positive indication (e.g., the "|" part of the "+" symbol) has a lower sensitivity such the reagents react only with samples containing a count of more than 10 WBC/HPF.

Another version of the subject device has text on the device in two places. In one place the text indicates a positive result. In another, it indicates a negative result. Next to the indications are matrices having the appropriate diagnostic test reagents. For example, next to the negative indication is a matrix having diagnostic test reagents that react with all samples. Next to the positive indication is a matrix having diagnostic test reagents that react only with samples that have more than 10 WBCS/HPF. The subject device, such as one of the examples above, does not require a chart, such as coloration chart, to interpret the results. This aspect of the invention makes the device (and the corresponding method) an even more rapid device (and method) for detecting prostatitis.

EXAMPLES

The following examples are included herein solely to aid in a more complete understanding of the invention disclosed and claimed herein. The Examples do not limit the scope of the invention in any fashion.

Test Example

The process for diagnosing prostatitis using the subject invention was tested on 297 clinic patients, the results of which are shown below in Table 1. For each patient, an EPS sample was obtained. The sample was subjected to testing via (1) the inventive dipstick method and (2) the conventional microscopic method. The results of the two tests were then compared. The dipstick method was performed with a MULTISTIX 2 dipstick to determine the leukocyte levels. The MULTISTIX-2 dipstick is sold as a dipstick for testing urine for pathological conditions such as kidney or urogenital tract infection or other dysfunction involving fluids. In the subject invention EPS was tested (instead of urine) for the presence or absence of prostatitis. The process for diagnosing prostatitis using EPS included the following steps:

1. A symptomatic patient's prostate (as defined by the Lower Tract Symptom Survey; reprinted below) was gently massaged, which caused the EPS to drip out of the tip of his penis.
2. The EPS was collected in a clean container. Alternatively, the EPS was placed on a substrate, such as a microscope slide. When placed on a microscope slide, the white blood cells in the EPS can be counted microscopically.
3. The tip of a MULTISTIX-2 dipstick by Bayer Aktiengesellschaft (Fed. Rep. Germany) was contacted with the prostatic secretion.
4. The dipstick was set aside for two minutes.
5. Next, the dipstick was read. The MULTISTIX-2 is read by evaluating a coloration change. The coloration change was compared to chart provided by Bayer which has the categories Negative, Trace, +1 (Small), +2 (Moderate) and +3 (Large). The coloration change can also be read as one of these categories, or as being between two of these categories (e.g., Between +1 and +2).

Symptomatic patients were selected with the Lower Tract Symptom Score, in which patients are surveyed on two difference dates. A yes or no answer was obtained for the following categories: Perineum Discomfort/Pain, Inguinal Discomfort/Pain, Lower Abdominal Discomfort/Pain, Scrotal Discomfort/Pain (Including Testicular), Penile Discomfort/Pain, Ejaculatory Discomfort/Pain, Dysuria (Pain/Stinging on Urination), Burning on Urination, Hematuria (Microscopic), Hematuria (Gross), Blood in Ejaculate (Per Patient) Decreased Sexual Performance (Per Patient).

The test results indicated that the EPS Negative patients (i.e., those patients scoring a Negative, Trace, or +1 (Small) with the dipstick) did not have prostatitis as determined by the microscopic method. In contrast, the EPS Positive patients (i.e., those patients scoring a Between +1 and +2, +2 (Moderate), Between +2 and +3, or +3 (Large) with the dipstick) had prostatitis as determined by the microscopic method. Thus, for this dipstick, using a result of a Negative, Trace, or +1 (Small) corresponded to the absence of prostatitis. In contrast, for this dipstick, using a result of a Between +1 and +2, +2 (Moderate), Between +2 and +3, or +3 (Large) corresponded to the presence of prostatitis. The results of this test showed that the dipstick test results correlated 97.5% with the results of the conventional microscopic examination. With these cut-offs and corresponding presence of prostatitis or absence of prostatitis defined for this dipstick, the need for a microscopic examination is eliminated; the test can be done more simply, rapidly, and with the same precision using the subject invention.

Dipsticks other than the MULTISTIX-2 can be used with equal success. For example the URISTIX-4 by Bayer, which detects leukocytes, protein, glucose, and nitrates, can be used. Likewise, the MULTISTIX-10, by Bayer, which detects leukocytes and nitrates, can also be used. If it is desired to use a different device, this type of study can be run to determine the cut-off points for the particular device. Therefore, it can be seen that the inventive method provides a useful, economical, and rapid method and device for detecting prostatitis.

Table 1 summarizes test result from 297 patients. Patient samples were tested for prostatitis using both the conventional microscope method and the subject method. The microscope results are entered as the number of WBCS/HPF. The microscope results are entered into the rows of the table from the top of the table to the bottom, and are placed in the column that corresponds to the dipstick result obtained on the same sample. For example, in the second column of row 1, a patient was entered that had between 2 and 4 WBCS/HPF found using the conventional microscope method. This same patient had a "trace" test result using the subject method. Therefore, the test result was placed in the second column. The double line between "Small +1" and "Between +1 and +2" denotes the point that was determined (for the MULTISTIX-2) to be the cutoff point between the absence of prostatitis and the presence of prostatitis.

TABLE 1

| EPS NEGATIVE | | | EPS POSITIVE | | | |
| --- | --- | --- | --- | --- | --- | --- |
| Scale | | | Scale | | | |
| Negative | | | Between +1 and +2 | | | |
| Trace | | | Moderate (+2) | | | |
| Small (+1) | | | Between +2 and +3 | | | |
| | | | Large (+3) | | | |
| Total Number of EPS Negative Patients 45 | | | Total Number of EPS Positive Patients 252 | | | |
| Negative | Trace | Small +1 | Between +1 and +2 | +2 (Moderate) | Between +2 and +3 | +3 (Large) |
| 4–7 | 2–4 | 6–8 | 25–35 | 100–120 | 20–30 | 80–100 |
| 1–4 | | 3–5 | 35–45 | 25–35 | 15–25 | TNTC* |
| 3–5 | | 8–12 | 50–150 | 10–30 | 35–50 | 40–60 |
| 0–2 | | 0–3 | 6–15 | 80–100 | 80–100 | 150–200 |
| 2–5 | | 8–12 | 5–15 | 2–50 | 5–35 | 10–35 |
| 8–100*** | | 3–5 | 10–15 | 15–25 | 50–100 | 80–120 |
| 3–6 | | 3–5 | 16–20 | 6–18 | 8–100 | 60–80 |
| 0–2 | | 5–10 | 6–25 | 30–70 | 8–100 | 25–40 |
| 0–3 | | 0–7 | 8–40 | 5-TNTC* | 8–18 | 75–150 |
| 7–15*** | | 4–8 | 12–25 | 25–40 | 35–50 | 30–50 |
| 0–2 | | 3–7 | 4–30 | 10–12 | 30–40 | 10–30 |
| | | | 0–6 | 2–30 | 12–20 | 15–25 | 40–60 |
| | | | 0–8 | 6–30 | 15–250** | 7–15 | 16–25 |
| | | | 1–3 | 3–35 | 3–20 | 80–120** | 80–150 |
| | | | 1–6 | 6–13 | 15–25 | 20–40 | 50–75 |
| | | | 3–5 | 5–35 | 10–20 | 5–19 | 60–150 |
| | | | 5–8 | 8–12 | 6–12 | 40–60 | 80–100 |
| | | | 0–2 | 40–60 | 12–15 | 12–25 | 100–300 |
| | | | 6–10 | 0–60 | 35–50 | 20–40 | 150–250 |
| | | | 2–4 | 15–25 | 10–18 | 7–11 | 120–140 |

TABLE 1-continued

| | | | | |
|---|---|---|---|---|
| 0–5 | 2–45 | 20–40 | 6–11 | 30–250 |
| 5–9 | 5–20** | 20–40 | 6–30 | 8–100 |
| 4–16*** | 8–16 | | 40–60 | 60–100 |
| 3–6 | 0–12 | | 40–60 | 30–40 |
| 3–8 | 4–16 | | 30–45 | 30–150 |
| 3–5 | 15–25 | | 2–12 | 60–200 |
| 2–15*** | 12–15 | | 20–200 | 60–120 |
| 3–5 | 6–18 | | 5–17 | 0–25 |
| 5–9 | 0–2*** | | 10–50 | 250–300 |
| 2–5 | 8–18 | | 10–30 | 150–200 |
| 4–25*** | 5–11 | | | 100–200 |
| 6–15 | 8–15 | | | 100–135 |
| 0–16*** | 25–45 | | | 35–300 |
| | 6–15 | | | 20–35 |
| | 80–125 | | | 25–40 |
| | 3–14 | | | 35–75 |
| | 10–25 | | | 30–135 |
| | 15–120 | | | 50–75 |
| | 15–25 | | | 80–125 |
| | 8–40 | | | 200–300 |
| | 12–20 | | | 100–125 |
| | 2–12 | | | 80–130 |
| | 6–15 | | | 120-TNTC* |
| | 6–12 | | | 200–300 |
| | 30–50 | | | 25–150 |
| | 10–15 | | | 50–150 |
| | 5–12 | | | 30-TNTC* |
| | 10–40 | | | 150–250 |
| | 15–40 | | | 60–100 |
| | 15–25 | | | 60–150 |
| | 10–15 | | | 30–40 |
| | 3–13 | | | 40–70 |
| | 2–12 | | | 20–75 |
| | | | | 35–45 |
| | | | | 100–150 |
| | | | | 60–100 |
| | | | | 20–50 |
| | | | | 300–400 |
| | | | | 40–80 |
| | | | | 100–120 |
| | | | | 8–25 |
| | | | | TNTC* |
| | | | | 80–125 |
| | | | | TNTC* |
| | | | | 25–45 |
| | | | | 25–45 |
| | | | | TNTC* |
| | | | | 40–60 |
| | | | | 70–120 |
| | | | | 30–40 |
| | | | | 50–70 |
| | | | | 60–80 |
| | | | | 40–60 |
| | | | | 60–100 |
| | | | | 20-TNTC* |
| | | | | 40–80 |
| | | | | 250-TNTC* |
| | | | | 200-TNTC* |
| | | | | 125–150 |
| | | | | TNTC* |
| | | | | 25–30 |
| | | | | 225–300 |
| | | | | 45–65 |
| | | | | TNTC* |
| | | | | 80–120 |
| | | | | 150–250 |
| | | | | 45-TNTC* |
| | | | | 100–125 |
| | | | | 60-TNTC* |
| | | | | 80–150 |
| | | | | 40–65 |
| | | | | 15–25 |
| | | | | 120–250 |
| | | | | 80–250 |
| | | | | 300-TNTC* |
| | | | | 40–60 |
| | | | | 40–65 |
| | | | | 15–25 |
| | | | | 45–65 |

TABLE 1-continued

| |
|---|
| 20–50 |
| 8–15 |
| 40–60 |
| 40–60 |
| 80–150 |
| 40–65 |
| 30–50 |
| 20–50 |
| 50–75 |
| 25–50 |
| 30–60 |
| 10–15 |
| 25–400 |
| 10–20 |
| 40–65 |
| 40–150 |
| 8–30 |
| 40–65 |
| 40–60 |
| 80–125 |
| 250–350 |
| 12–30 |
| 35–50 |
| 35–50 |
| 50-TNTC* |
| 200–350 |
| 80–150 |
| 50–70 |
| 40–70 |
| 25–75 |

Total Number of Patients in Each Group

| | | | | | | |
|---|---|---|---|---|---|---|
| 11 | 1 | 33 | 53 | 22 | 30 | 129 |

*TNTC = too numerous to count (>500 WBCS/HPF)
**Clumps present in sample
***Different diagnosis on dipstick than on microscope Results obtained using the method described herein correlated 97.5% with results obtained through the conventional microscope method. Of the 2.5% of the result that did not have the subject method results correlate with the conventional method results, six of the 297 patients were negative using the subject method but were positive using the conventional method. One of 297 patients was positive using the subject method but was negative using the conventional method. The remaining 290 patients had subject method results that correlated with the conventional method results. That is, in 290 patients when the dipstick indicated the absence of prostatitis, so did the conventional method and when the dipstick indicated the presence of prostatitis, so did the conventional method.

The importance testing EPS as opposed to a body fluid in detecting prostatitis is demonstrated in the following examples.

Patient No. 1

A 42-year-old patient's EPS and ejaculate were tested for prostatitis to compare the results produced using EPS as a test sample verses using ejaculate. Both samples were tested using the subject invention with the MULTISTIX-2 and were confirmed with the conventional microscope method. The EPS was tested using the subject invention as described above. The patient's ejaculate was also tested using the subject invention except that ejaculate was substituted for the EPS. Both the EPS and ejaculate were also tested using the conventional microscopic determination of the number of white blood cells per high powered field (WBCS/HPF). The patient was 28 days post-vasectomy. When the ejaculate was tested with the subject invention, the dipstick result was negative, and when the ejaculated was microscopically examined, it contained 1–5 WBCS/IPF. Because this result was under 10, a diagnosis of negative evidence of prostatitis would normally be assigned. However, when the EPS was examined with the subject invention, the EPS was +3, and when the EPS was examined microscopically, it had 10–18 WBCS/HPF. Because the dipstick testing the EPS indicated prostatitis and the microscope white blood cell count was over 10 in the EPS, a diagnosis of prostatitis was assigned. The subject method, which tests EPS, was confirmed by counting the WBC/HPF using the conventional microscopic examination. Thus, the diagnosis so prostatitis is more accurate when using EPS than when using ejaculate.

This shows that the EPS is a true representation of the prostate's health. With the more accurate diagnosis provided by the subject invention, patients can be diagnosed and treated in more instances than they could be with previous methods.

Patient No. 2

A 32-year-old post-vasectomy patient was tested for the presence of prostatitis using ejaculate, urine, and EPS as test samples to compare the results obtained using EPS as a test sample verses using ejaculate and urine. All samples were tested using the subject invention with the MULTISTIX-2 and were confirmed with the conventional microscope method. For the subject invention, EPS was tested with the method described above. The ejaculate and urine were tested using the steps of the subject invention except that the ejaculate and urine were substituted for the EPS. The ejaculate showed 0–3 WBCS/HPF by conventional microscopic examination, with the dipstick being negative. A urinalysis yielded 0–3 WBCS/HPF by conventional microscopic examination, with the dipstick being negative. Thus, testing the ejaculate and the urine resulted in the absence of detection of prostatitis. In contrast, when the EPS was tested, it showed 25–45 WBCS/HPF by microscopic examination, with the dipstick being +3 (Large). Thus, testing the EPS permitted the identification of prostatitis, and the patient could be treated for this disease state.

This is in stark contrast to conventional methods in which attempts to culture ejaculate were made when white blood cells were found in ejaculate. However, this normally resulted in no growth. This being the case, conventional methods would have stopped here. Thus, previous methods would fail to detect prostatitis in patients in which negative test results were obtained on the ejaculate, such as the conventional microscope method. Likewise, if conventional culture results on ejaculate were negative, a patient was not diagnosed as having prostatitis. In contrast, by testing EPS instead of ejaculate or urine, the subject method resulted in an accurate detection of the presence of prostatitis.

The invention is not limited to the particular reagents, protocols, and embodiments described herein above, but includes all modified and equivalent forms thereof which are within the scope of the following claims.

What is claimed is:

1. A method of detecting prostatitis comprising:
   (a) obtaining an expressed prostatic secretion from a patient;
   (b) contacting a device having diagnostic test reagent to the expressed prostatic secretion for a period of approximately two minutes to detect white blood cells in the expressed prostatic secretion, wherein the diagnostic test reagent on the device is present in an amount sufficient to generate a positive indication when the number of white blood cells per high powered field is greater than 10 and a negative indication when the number of white blood cells per high powered field is 10 or less; and
   (c) determining the presence of prostatitis with the positive indication and the absence of prostatitis with the negative indication.

2. The method of claim 1, wherein in step (b) the device contacted is selected from the group consisting of card, a pad, a strip, and a dipstick.

3. The method of claim 1, wherein in step (b) the device contacted has diagnostic test reagents that detect leukocytes or a leukocyte enzyme.

4. The method of claim 3, wherein in step (b) the device contacted has diagnostic test reagents that detect a leukocyte enzyme selected from the group consisting of a leukocyte esterase, an esterolytic enzyme and a proteolytic enzyme.

5. The method of claim 1, wherein in step (b) the reacting produces a visual change.

6. A device for detecting prostatitis from an expressed prostatic secretion according to the method of claim 1 using a dipstick comprising:
   (a) a matrix having diagnostic test reagents that react with the expressed prostatic secretion by detecting leukocytes or a leukocyte enzyme, wherein the diagnostic test reagents are present in an amount sufficient to generate a positive indication when the number of white blood cells per high powered field is greater than 10 in the expressed prostatic secretion, and wherein the diagnostic test reagents generate a negative indication when the number of white blood cells per high powered field is 10 or less in the expressed prostatic secretion;
   (b) a mounting substrate, wherein the matrix is attached to the mounting substrate,
      wherein the device determines the presence of prostatitis with the positive indication and the absence of prostatitis with the negative indication.

7. The device of claim 6, wherein the device is selected from the group consisting of a card, a pad, a strip, and a dipstick.

8. The device of claim 7, wherein the matrix comprises filter paper.

9. The device of claim 6, wherein the diagnostic test reagents are associated with the matrix through a process selected from the group consisting of impregnation, coating, linking, and covalent attachment.

10. The device of claim 6, wherein the leukocyte enzyme is selected from the group consisting of a leukocyte esterase, an esterolytic enzyme, and a proteolytic enzyme.

11. The device of claim 6, wherein the diagnostic test reagents comprise an ester and a diazonium salt.

12. The device of claim 11, wherein the ester is a chromogenic ester.

13. The device of claim 6, wherein the diagnostic test reagents comprise a derivatized pyrrole amino acid ester, a diazonium salt, a buffer, and non-reactive ingredients.

14. The device of claim 13, wherein the diagnostic test reagents comprise about 0.4% w/w derivatized pyrrole amino acid ester, about 0.2% w/w diazonium salt, about 40.9% w/w buffer, and about 58.5% w/w non-reactive ingredients.

* * * * *